United States Patent
Duindam et al.

(10) Patent No.: US 11,678,813 B2
(45) Date of Patent: Jun. 20, 2023

(54) SYSTEMS AND METHODS FOR DEFORMATION COMPENSATION USING SHAPE SENSING

(71) Applicant: Intuitive Surgical Operations, Inc., Sunnyvale, CA (US)

(72) Inventors: Vincent Duindam, San Francisco, CA (US); Prashant Chopra, Foster City, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 13 days.

(21) Appl. No.: 17/240,154

(22) Filed: Apr. 26, 2021

(65) Prior Publication Data

US 2021/0282662 A1     Sep. 16, 2021

Related U.S. Application Data

(60) Continuation of application No. 16/114,456, filed on Aug. 28, 2018, now Pat. No. 11,026,594, which is a
(Continued)

(51) Int. Cl.
*A61B 5/00* (2006.01)
*A61B 5/06* (2006.01)
(Continued)

(52) U.S. Cl.
CPC ............ *A61B 5/066* (2013.01); *A61B 5/0044* (2013.01); *A61B 5/062* (2013.01); *A61B 5/065* (2013.01);
(Continued)

(58) Field of Classification Search
None
See application file for complete search history.

(56) References Cited

U.S. PATENT DOCUMENTS

| 6,380,732 B1 | 4/2002 | Gilboa |
| 6,389,187 B1 | 5/2002 | Greenaway et al. |

(Continued)

FOREIGN PATENT DOCUMENTS

| CN | 1725029 A | 1/2006 |
| CN | 101076282 A | 11/2007 |

(Continued)

OTHER PUBLICATIONS

Extended European Search Report for Application No. 13791486.7, dated Jul. 12, 2016, 11 pages.
(Continued)

*Primary Examiner* — Joel F Brutus
(74) *Attorney, Agent, or Firm* — Haynes and Boone, LLP

(57) ABSTRACT

A method and medical system for estimating the deformation of an anatomic structure that comprises generating a first model of at least one anatomical passageway from anatomical data describing a patient anatomy and determining a shape of a device positioned within the branched anatomical passageways. The method and medical system also comprise generating a second model of the plurality of branched anatomical passageways by adjusting the first model relative to the determined shape of the device.

20 Claims, 10 Drawing Sheets

Related U.S. Application Data division of application No. 13/893,008, filed on May 13, 2013, now Pat. No. 10,085,671.

(60) Provisional application No. 61/646,669, filed on May 14, 2012.

(51) Int. Cl.
  *A61B 34/30* (2016.01)
  *G16Z 99/00* (2019.01)
  *A61B 17/00* (2006.01)
  *A61B 34/10* (2016.01)
  *A61B 34/20* (2016.01)

(52) U.S. Cl.
  CPC .............. *A61B 34/30* (2016.02); *G16Z 99/00* (2019.02); *A61B 2017/00699* (2013.01); *A61B 2017/00809* (2013.01); *A61B 2034/105* (2016.02); *A61B 2034/2051* (2016.02); *A61B 2034/2061* (2016.02); *A61B 2034/301* (2016.02); *A61B 2034/303* (2016.02); *A61B 2505/05* (2013.01); *A61B 2562/043* (2013.01)

(56) References Cited

U.S. PATENT DOCUMENTS

| | | | |
|---|---|---|---|
| 7,930,065 | B2 | 4/2011 | Larkin et al. |
| 10,085,671 | B2 | 10/2018 | Duindam et al. |
| 11,026,594 | B2 | 6/2021 | Duindam et al. |
| 2004/0045561 | A1* | 3/2004 | Alexander ........... G09B 23/285 128/897 |
| 2005/0180389 | A1 | 8/2005 | Xenakis et al. |
| 2005/0182295 | A1 | 8/2005 | Soper et al. |
| 2006/0013523 | A1 | 1/2006 | Childlers et al. |
| 2008/0118135 | A1 | 5/2008 | Averbuch et al. |
| 2008/0171934 | A1 | 7/2008 | Greenan et al. |
| 2008/0285909 | A1 | 11/2008 | Younge et al. |
| 2009/0227861 | A1 | 9/2009 | Ganatra et al. |
| 2010/0249506 | A1 | 9/2010 | Prisco |
| 2011/0019878 | A1 | 1/2011 | Soubelet et al. |
| 2011/0092793 | A1 | 4/2011 | Thomson et al. |
| 2012/0059220 | A1* | 3/2012 | Holsing ................. A61B 5/061 600/117 |
| 2012/0289777 | A1 | 11/2012 | Chopra et al. |
| 2013/0303891 | A1 | 11/2013 | Chopra |
| 2013/0303894 | A1 | 11/2013 | Duindam et al. |
| 2019/0008413 | A1 | 1/2019 | Duindam et al. |

FOREIGN PATENT DOCUMENTS

| | | |
|---|---|---|
| CN | 101765864 A | 6/2010 |
| CN | 101925924 A | 12/2010 |
| CN | 101961245 A | 2/2011 |
| CN | 102272799 A | 12/2011 |
| CN | 102346811 A | 2/2012 |
| JP | 2001170027 A | 6/2001 |
| JP | 2007083038 A | 4/2007 |
| JP | 2008194475 A | 8/2008 |
| JP | 2010510815 A | 4/2010 |
| WO | WO-03083779 A3 | 12/2003 |
| WO | WO-2008076910 A1 | 6/2008 |
| WO | WO-2009147683 A1 | 12/2009 |
| WO | WO-2010105197 A2 | 9/2010 |
| WO | WO-2010111090 A1 | 9/2010 |
| WO | WO-2011163630 A1 | 12/2011 |
| WO | WO-2012001548 A1 | 1/2012 |
| WO | WO-2012025856 A1 | 3/2012 |

OTHER PUBLICATIONS

Extended European Search Report for Application No. 18208173.7 dated Mar. 27, 2019, 7 pages.

International Search Report and Written Opinion for Application No. PCT/US2013/040780, dated Aug. 12, 2013, 12 pages.

LAN/MAN Standards Committee, "Part 11: Wireless LAN Medium Access Control (MAC) and Physical Layer (PHY) Specifications," IEEE Standard for Information technology, Telecommunications and Information Exchange Between Systems, Local and Metropolitan Area Networks, Specific Requirements, IEEE Std 802.11-2012 (Revision of IEEE Std 802.11-2007), IEEE Computer Society, Mar. 29, 2012, 2793 pages.

Office Action dated Feb. 10, 2017 for Chinese Application No. 201380025063.6 filed Mar. 18, 2013, 15 pages.

Office Action dated Feb. 21, 2017 for Japanese Application No. 2015512721 filed May 13, 2013, 8 pages.

Partial Supplementary European Search Report for Application No. 13791486.7, dated Mar. 22, 2016, 8 pages.

U.S. Appl. No. 60/588,336, inventor Childers; Brooks A., filed on Jul. 16, 2004.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR DEFORMATION COMPENSATION USING SHAPE SENSING

CROSS-REFERENCE TO RELATED APPLICATIONS

This application is a continuation of U.S. patent application Ser. No. 16/114,456 filed Aug. 28, 2018, which is a divisional application of U.S. patent application Ser. No. 13/893,008 filed May 13, 2013 [now issued as U.S. Pat. No. 10,085,671], which claims the benefit of U.S. Provisional Application No. 61/646,669 filed May 14, 2012, which are incorporated by reference herein in their entirety.

FIELD

The present disclosure is directed to systems and methods for tracking a medical device within a patient anatomy during a medical procedure, and more particularly to systems and methods for efficiently tracking a medical device within a patient anatomy using a shape sensor.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of shape sensors to more accurately describe the shape, pose, and location of the surgical instrument in real space or with respect to pre-procedural or concurrent images. In a dynamic anatomical system and/or in an anatomical region dense with many anatomical passageways, accurately registering the minimally invasive instrument to the anatomical system is a time consuming and processing intensive task. Improved systems and methods are needed for increasing the accuracy and efficiency of systems and methods of registering minimally invasive instruments to the anatomical system.

SUMMARY

The embodiments of the invention are summarized by the claims that follow below.

In one embodiment, a method comprises generating a first model of at least one anatomical passageway from anatomical data describing a patient anatomy and determining a shape of a device positioned within the branched anatomical passageways. The method also comprises generating a second model of the plurality of branched anatomical passageways by adjusting the first model relative to the determined shape of the device.

In another embodiment, a medical system comprises a flexible device including a shape sensor, a memory storing anatomical data describing a patient anatomy; and a processor. The processor generates a first model of a plurality of branched anatomical passageways from the anatomical data describing a patient anatomy and receives information from the shape sensor to determine a shape of the device positioned within the branched anatomical passageways. The processor also generates a second model of the plurality of branched anatomical passageways by adjusting the first model relative to the shape of the device.

In another embodiment, a method comprises generating a first model of a plurality of branched anatomical passageways from anatomical data describing a patient anatomy recorded while the branched anatomical passageways are in a first state of an alternating movement. The method also comprises generating a second model of the plurality of branched anatomical passageways from anatomical data describing a patient anatomy recorded while the branched anatomical passageways are in a second state of the alternating movement. The method also comprises generating a first image of an device positioned within the branched anatomical passageways in a first shape when the branched anatomical passageways are in the first state and generating a second image of the device positioned within the branched anatomical passageways in a second shape when the branched anatomical passageways are in the second state.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 10:
Figure 10:
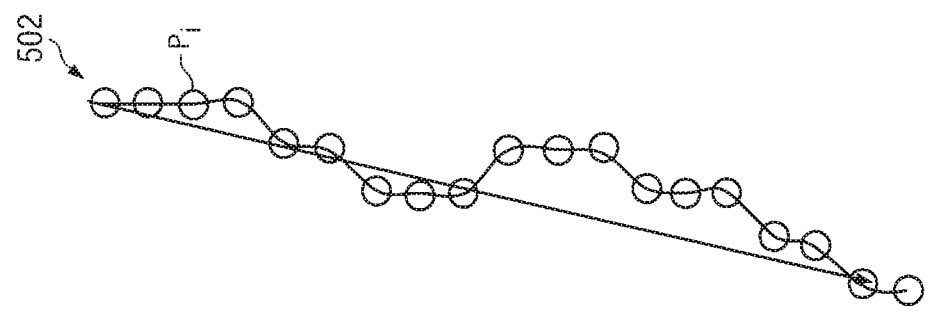
Figure 10:
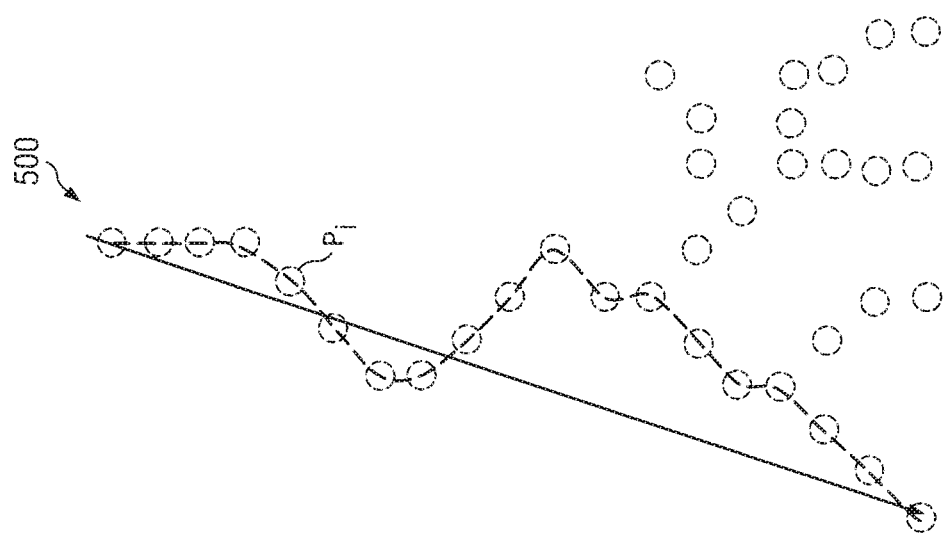

FIG. 10 includes illustrations of a models of an anatomical passageway according to another embodiment of the disclosure.

Figure 11:
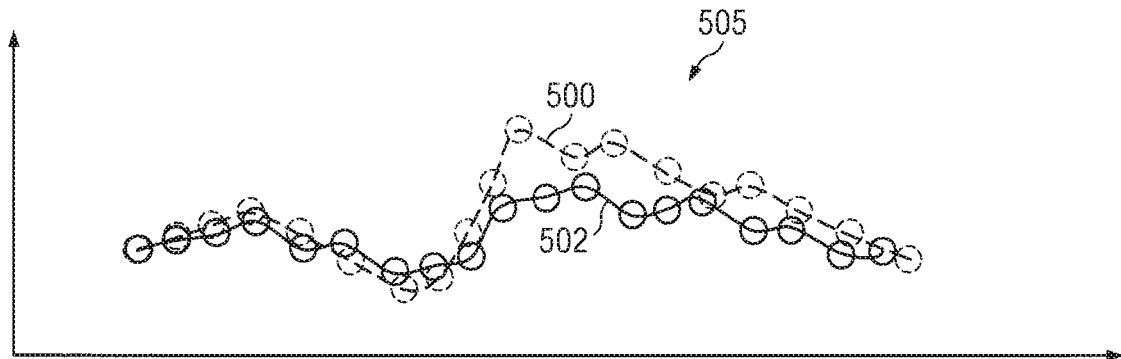

FIG. 11 is a histogram for matching the model of FIG. 10.

Figure 12:
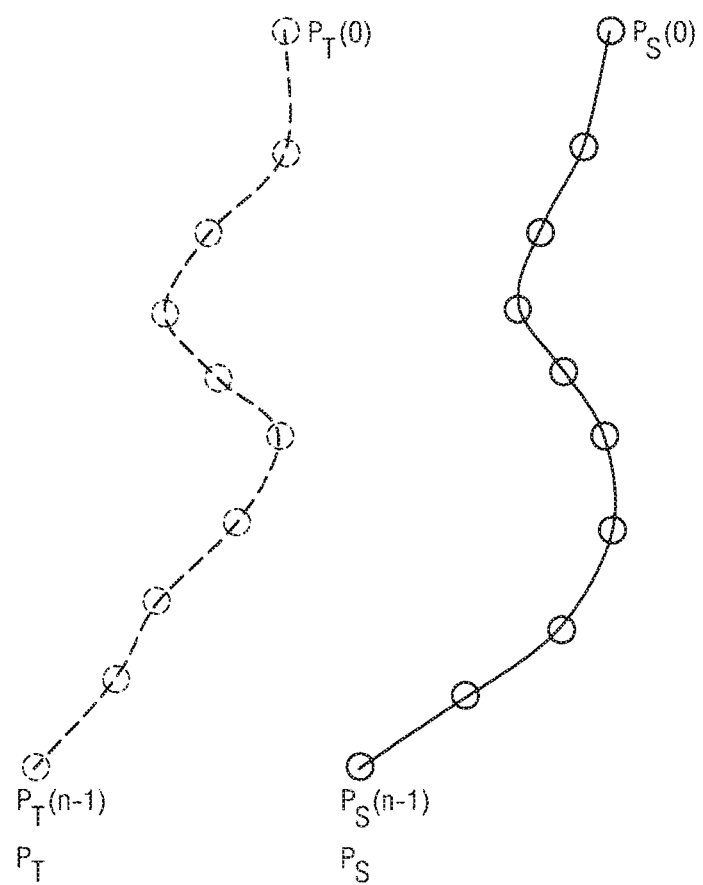

FIG. 12 illustrates point sets used to determine a transformation.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y,Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
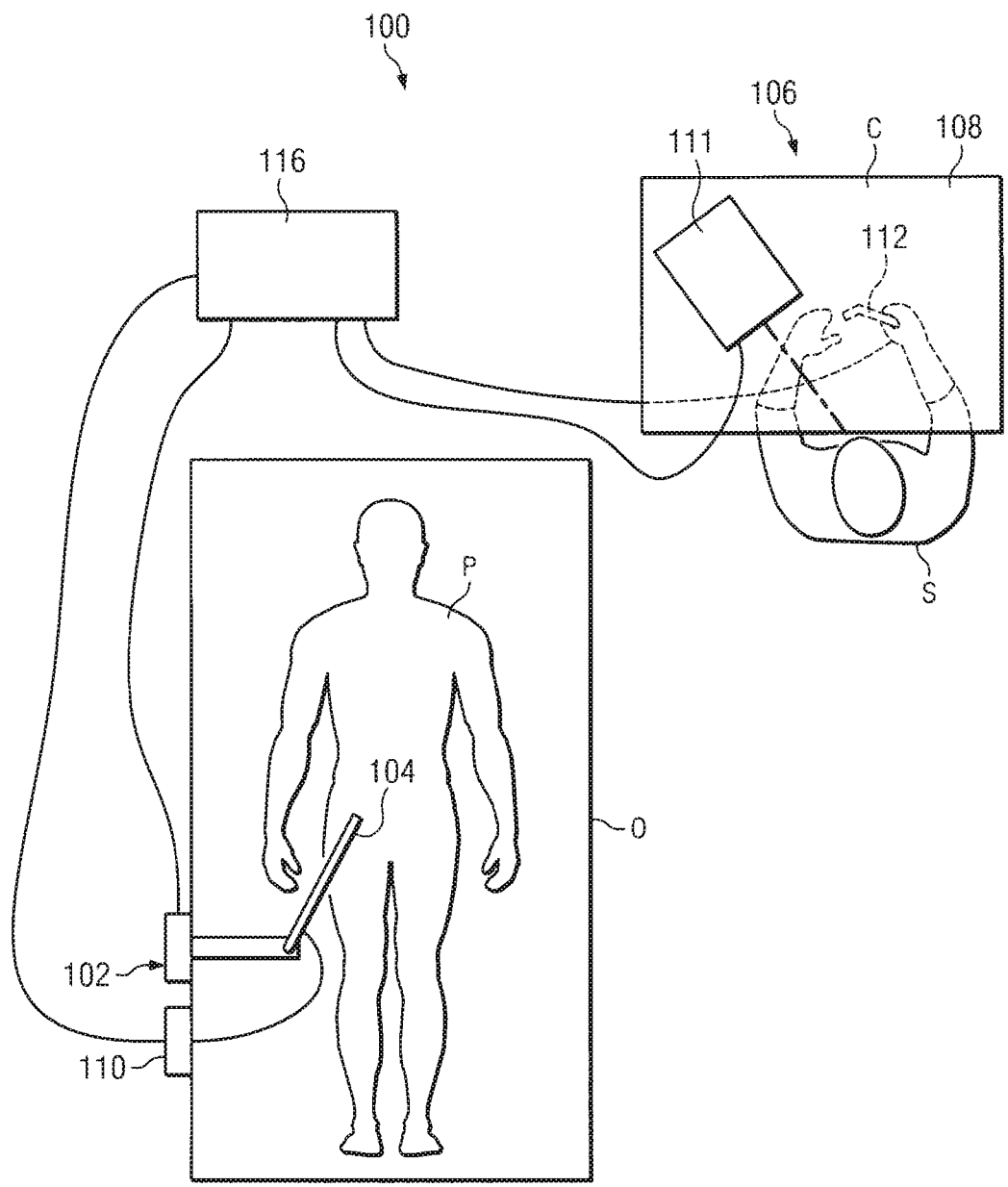
FIG. 1 is a robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the surgeon S to view the surgical site and to control the manipulator assembly 102.

In alternative embodiments, the robotic system may include more than one manipulator assembly. The exact number of manipulator assemblies will depend on the surgical procedure and the space constraints within the operating room among other factors.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the surgeon with telepresence, or the perception that the control device(s) 112 are integral with the instruments 104 so that the surgeon has a strong sense of directly controlling instruments 104. In some embodiments, the control devices 112 are manual input devices which move with six degrees of freedom, and which may also include an actuatable handle for actuating instruments (for example, for closing grasping jaws, applying an electrical potential to an electrode, delivering a medicinal treatment, or the like).

A visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 100 includes endoscopic components that may be integrally or removably coupled to the surgical instrument 104. However in alternative embodiments, a separate endoscope, attached to a separate manipulator assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

A display system 111 may display an image of the surgical site and surgical instruments captured by the visualization system 110. The display 111 and the master control devices 112 may be oriented such that the relative positions of the imaging device in the scope assembly and the surgical instruments are similar to the relative positions of the surgeon's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the surgical instruments 104.

Alternatively or additionally, monitor 111 may present images of the surgical site recorded and/or modeled preoperatively using imaging technology such as, computerized tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images.

In some embodiments, the monitor 111 may display a virtual navigational image in which the actual location of the surgical instrument is registered (i.e., dynamically referenced) with preoperative or concurrent images to present the surgeon S with a virtual image of the internal surgical site at the location of the tip of the surgical instrument. An image of the tip of the surgical instrument or other graphical or alphanumeric indicators may be superimposed on the virtual image to assist the surgeon controlling the surgical instrument. Alternatively, the surgical instrument may not be visible in the virtual image.

In other embodiments, the monitor 111 may display a virtual navigational image in which the actual location of the surgical instrument is registered with preoperative or concurrent images to present the surgeon S with a virtual image of surgical instrument within the surgical site from an external viewpoint. An image of a portion of the surgical instrument or other graphical or alphanumeric indicators may be superimposed on the virtual image to assist the surgeon controlling the surgical instrument.

As shown in FIG. 1, a control system 116 includes at least one processor and typically a plurality of processors for effecting control between the surgical manipulator assembly 102, the master assembly 106, and the image and display system 110. The control system 116 also includes software programming instructions to implement some or all of the methods described herein. While control system 116 is shown as a single block in the simplified schematic of FIG. 1, the system may comprise a number of data processing circuits (e.g., on the surgical manipulator assembly 102 and/or on the master assembly 106), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instruments 104 to the hand-operated control device 112. Any suitable conventional or specialized servo controller may be used. A servo controller may be separate from, or integral with manipulator assemblies 102. In some embodiments, the servo controller and manipulator assembly are provided as part of a robotic arm cart positioned adjacent to the patient's body. The servo controller transmits signals instructing the manipulator assemblies to move instruments which extend into an internal surgical site within the patient body via openings in the body.

Each of the manipulator assemblies 102 that support a surgical instrument 104 and may comprise a series of manually articulatable linkages, generally referred to as set-up joints, and a robotic manipulator. The robotic manipulator assemblies 102 may be driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom that may include three degrees of linear motion (e.g., X, Y, Z linear motion) and three degrees of rotational motion (e.g., roll, pitch, yaw). Additionally, the motors can be used to actuate an articulatable end effector of the instrument for grasping tissues in the jaws of a biopsy device or the like.

Figure 2:
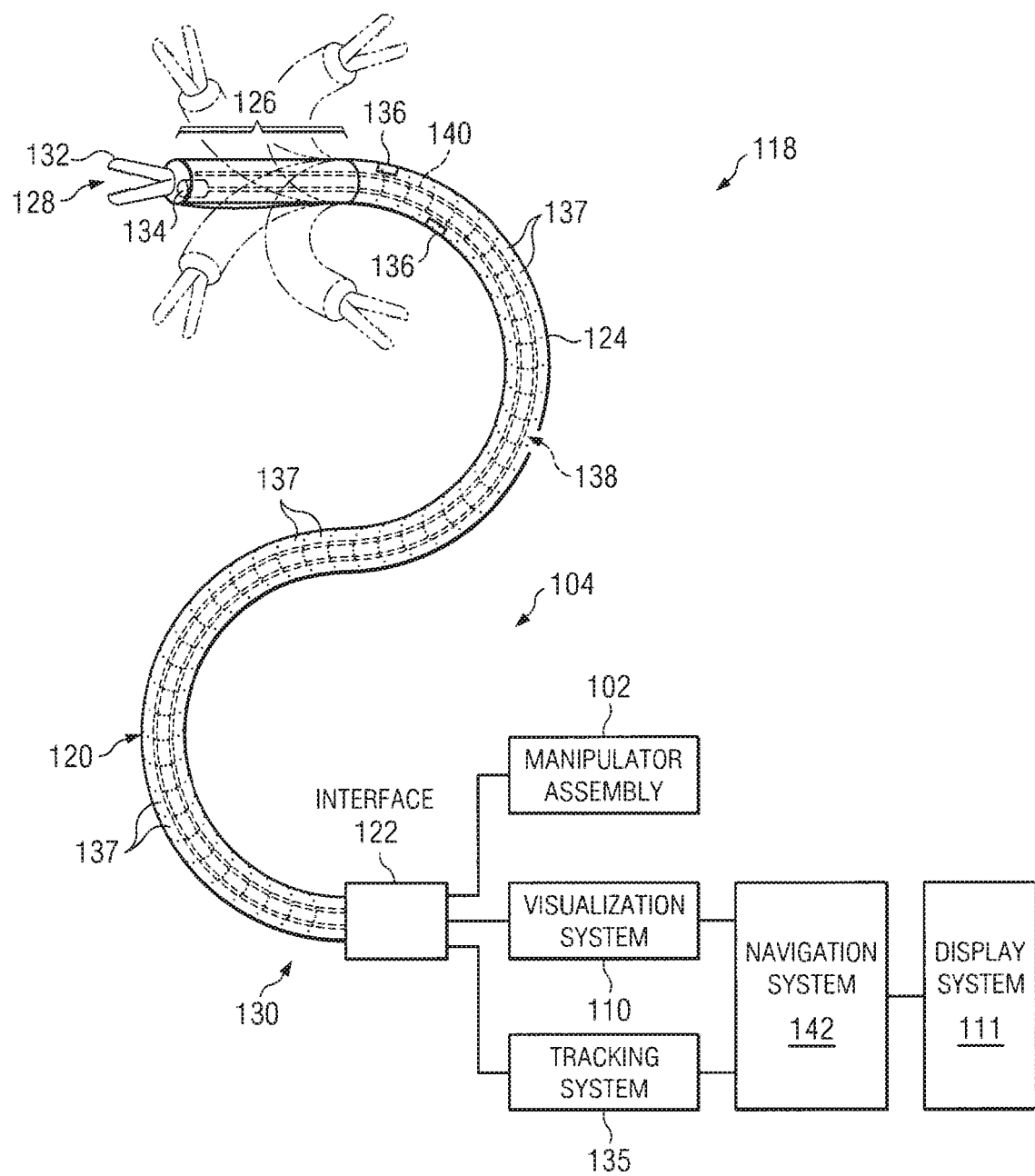
FIG. 2 illustrates a surgical instrument system utilizing aspects of the present disclosure.

FIG. 2 illustrates a tracked instrument system 118 which includes the surgical instrument system 104 and its interfacing systems. The surgical instrument system 104 includes a flexible instrument 120 coupled by an interface 122 to manipulator assembly 102 and visualization system 110. The instrument 120 has a flexible body 124, a tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The flexible instrument may be steerable, including the steering controls previously described, or may be non-steerable with no integrated mechanism for operator control of the instrument bending. The end effector may be a working distal part that is manipulable for a medical function, e.g., for effecting a predetermined treatment of a target tissue. For instance, some end effectors have a single working member such as a scalpel, a blade, or an electrode. Other end effectors such as shown in the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which surgical instruments can be deployed and used at a target surgical location.

The instrument 120 can also include an image capture element 134 which may include a stereoscopic or monoscopic camera disposed at the distal end 128 for capturing images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 135 includes an electromagnetic (EM) sensor system 136 and a shape sensor system 138 for determining the position, orientation, speed, pose, and/or shape of the distal end 128 and of one or more segments 137 along the instrument 120. Although only an exemplary set of segments 137 are depicted in FIG. 2, the entire length of the instrument 120, between the distal end 128 and the proximal end 130 and including the tip 126 may be effectively divided into segments. The tracking system 135 may be implemented as hardware, firmware, software or a combination thereof which interact with or are otherwise executed by one or more computer processors, which may include the processors of a control system 116.

The EM sensor system 136 includes one or more conductive coils that may be subjected to an externally generated electromagnetic field. Each coil of the EM sensor system 136 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 μm. In other embodiments, the dimensions may be larger or smaller.

The optical fiber 140 forms a fiber optic bend sensor for determining the shape of the instrument 120. In one alternative, optical fibers including Fiber Bragg Gratings (FBGs) are used to provide strain measurements in structures in one or more dimensions. Various systems and methods for monitoring the shape and relative position of a optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as EM sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding 146. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber 140 is used to monitor the shape of at least a portion of the instrument 120. More specifically, light passing through the optical fiber 140 is processed by the tracking system 135 for detecting the shape of the surgical instrument 120 and for utilizing that information to assist in surgical procedures. The tracking system 135 may include a detection system for generating and detecting the light used for determining the shape of the instrument 120. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images to provide the surgeon or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 104 is teleoperated within the robotic surgical system 100. In an alternative embodiment, the manipulator assembly may be replaced by direct operator control. In the direct operation alternative, various handles and operator interfaces may be included for hand-held operation of the instrument.

Figure 3B:
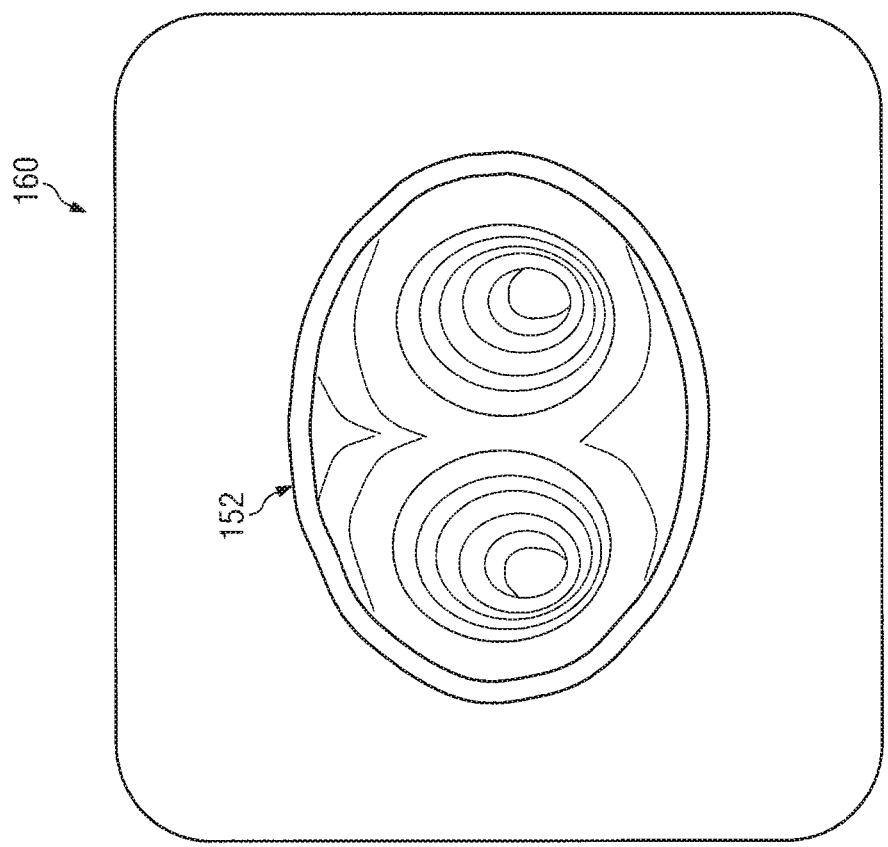
FIG. 3b is an internal image of the human lung depicting the region of the human lung from the viewpoint of the minimally invasive instrument.
Figure 3A:
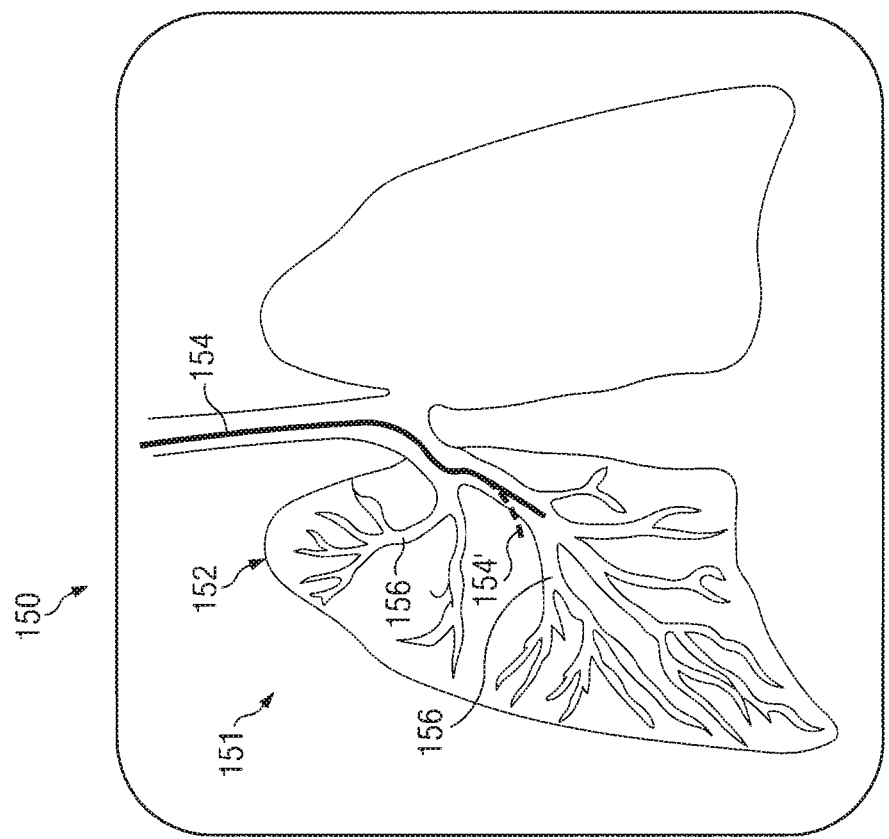
FIG. 3a is an image of a human lung registered with an image of a minimally invasive instrument.

FIG. 3a depicts a composite image 150 including an image 151 of a human lung 152, from a viewpoint external to the lung, registered with an instrument image 154 of a flexible instrument, such as the flexible instrument 120. The image 151 of the lung 152 may be generated from preoperatively recorded images or may be generated concurrently during the surgical procedure. The composite image 150 may be displayed via display system 111. As the instrument 120 is advanced through bronchial passageways 156 of the lung 152, information from the tracking system 135 and/or the visualization system 110 is used to register the instrument image 154 with the lung image 151. The image 151 of the lung 152 may change, for example, to depict the lung in a state of inspiration or expiration. The instrument image 154 may change to depict the advancement or withdrawal of the instrument 120 through the bronchial passageways 156. Occasionally, the composite image 150 may erroneously render the instrument image 154 such that a portion of the instrument image 154' is outside of a bronchial passageway. Systems and methods are described below for correcting the instrument image such that the instrument is located within the bronchial passageways.

FIG. 3b is an internal image 160 of the human lung 152 depicting a region of the lung from the viewpoint of the instrument 120. The image 160 may be a concurrent image taken during the surgical procedure by the instrument 120 while located in the depicted portion of the lung 152. More specifically, the image may be captured by the visualization system 110. Alternatively, the image 160 may be a preoperatively recorded image selected based upon the location of the tip of the instrument 120 as determined by the tracking system 135.

Often, the tracking system 135, which includes the EM sensor system 136 and the shape sensor system 138 may calculate a position for the instrument tip 126 or one or more segments 137 of the instrument 120 that is outside the anatomical passageway. This likely indicates a slight measurement error (assuming the wall of the anatomical passageway has not been breached). Such an error may result from the dynamic nature of certain anatomic structures such as the lungs or the heart. For example, inhalation and exhalation changes the position and size of the bronchial passageways of the lung. Alternatively, the error may result from patient motion or from tissue deformation caused by the presence of the surgical instrument within the anatomic passageways. To correct the position of the instrument and accurately locate one or more points of the instrument within the passageway when the image of the instrument and the image of the patient anatomy are co-registered and displayed, selected points of the instrument may be snapped or graphically registered to a location on the wall of the anatomical passageway or to the lumen of the anatomical passageway. As will be described in detail below, a variety of compensation methods may be used to correct the model of the patient anatomy to adjust for internal and external deformation forces, patient movement, or other changes in the patient anatomy subsequent to the recording of the preoperative image. Internal deformation forces on tissues of the anatomy may result, for example, from movement between breathing states of inspiration and expiration, cardiac movement, and coughing. External deformation forces on tissues of the anatomy may result, for example, from instrument insertion and manipulation. A corrected model of the patient anatomy allows for the generation of a more accurate composite image of the instrument relative to the anatomical passageways.

A corrected model may be particularly useful in the context of virtual navigation inside the anatomical passageways of a patient. Virtual navigation is based upon reference to a pre-operatively acquired dataset associated with the three dimensional anatomical structure of the passageways. For example, the dataset may be acquired by a preoperative CT scan. Software is used to convert the CT images into a three dimensional model describing the various locations and shapes of the passageways and their connectivity. During the virtual navigation procedure, the sensor system, particularly the EM sensor system, may be used to compute an approximate location of the instrument with respect to the patient anatomy. Typically an assumption is made that all parts of the patient anatomy are fixed with respect to each other. Under this assumption, a virtual view from the location of the tip of the instrument inside the patient anatomy, similar to the view in FIG. 3b, can be computed from the preoperative CT scan dataset. As previously described, the assumption that the patient anatomy remains fixed is generally invalid due to various deformation forces applied to the patient anatomy. To compensate for the motion or other errors introduced by the sensor system, a virtual view may be generated from the closest point to the sensed location of the tip of the instrument, inside the passageway, rather than from the computed position of the tip of the instrument. The process of adjusting the location of the sensed location of the instrument to an adjusted location within or on the wall of a passageway is known as snapping. Snapping may work particularly well when passageways are well separated and not densely packed. When deformation forces are large and the passageways are dense, snapping alone may result in an incorrect choice for the airway in which the instrument is located.

Figure 4B:
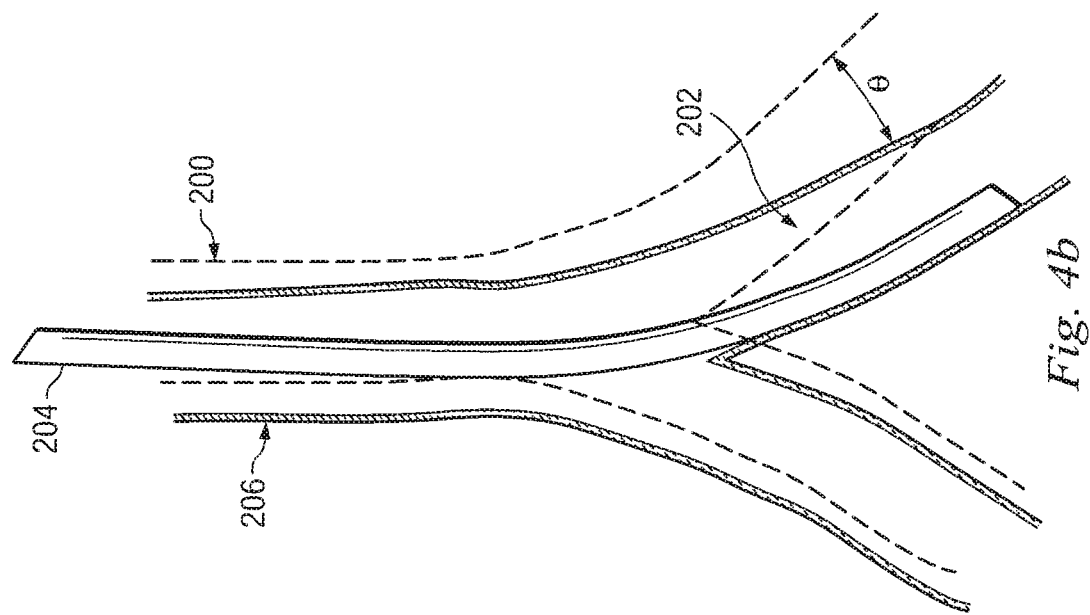
FIG. 4b is an illustration of the model of FIG. 4a adjusted based upon deformation forces applied by the catheter.
Figure 4A:
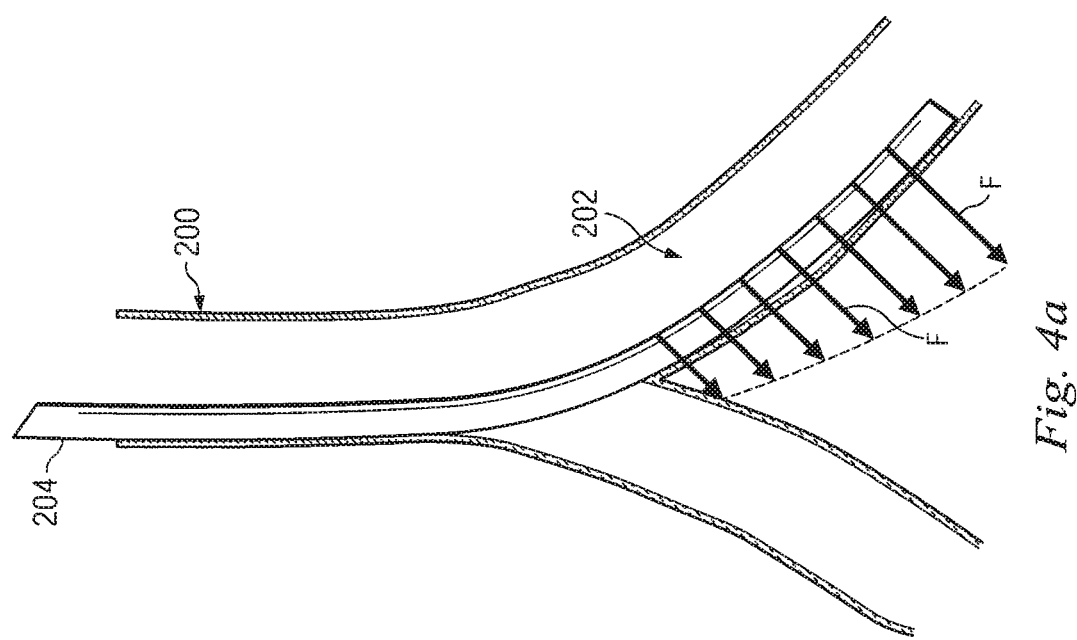
FIG. 4a is an illustration of model of a bronchial passageway of a lung with a catheter.

FIG. 4a is an illustration of an undeformed model 200 of a bronchial passageway 202 of a lung. A catheter 204 extends into the bronchial passageway 202. The catheter 204 may be substantially similar to the instrument 120. The model 200 may be displayed on a display system or may reside in an undisplayed form in a computer memory. As shown, the catheter 204 exerts deformation forces F on the bronchial passageway 202. FIG. 4b illustrates the effect of the deformation forces F on the model 160. The forces F of the catheter 204 move the bronchial passage 202 an angle θ. A deformed model 206 illustrates the effect of the forces of the catheter 164 on location and orientation of the bronchial passageway 202.

Figure 5A:
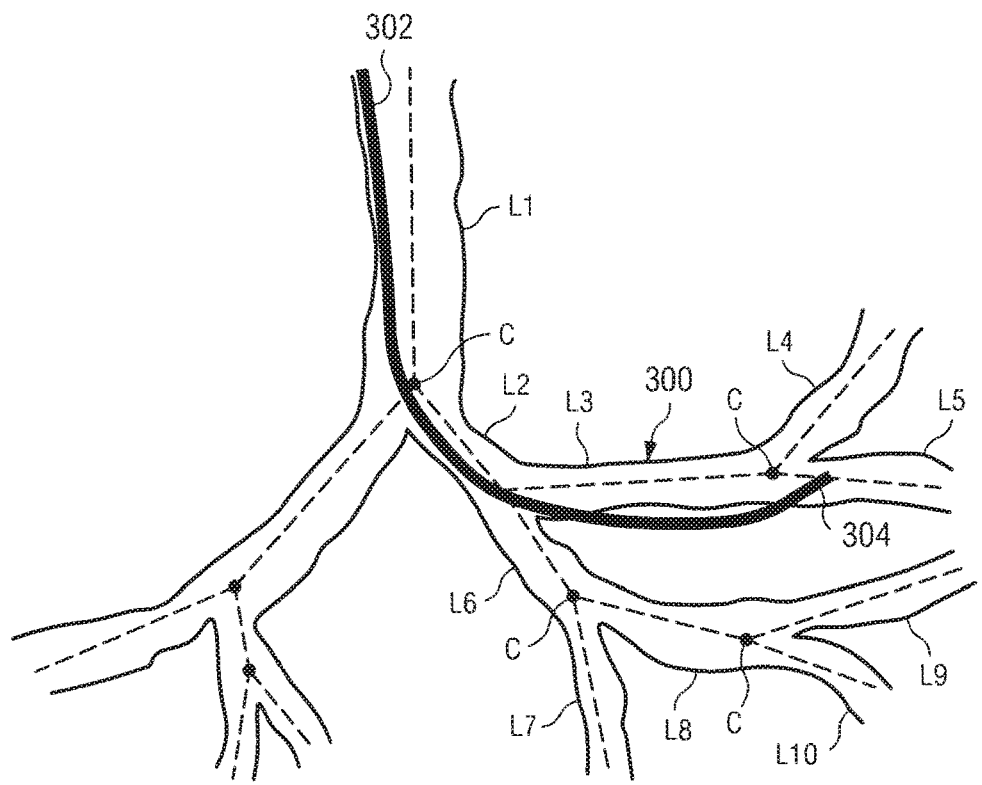
FIG. 5a illustrates a composite image of an undeformed model of a bronchial passageway and a catheter.

FIG. 5a illustrates a composite image of an undeformed model 300 of a branched structure of bronchial passageways and a catheter 302 extending through the passageways. With the undeformed model 300, a tip 304 of the catheter 302 appears, in the composite image, to be located within the bronchial passageway L5 rather than in passageway L4.

As shown in FIG. 5a, the bronchial passageways are modeled as a set of rigid links L1-L10 connected by joints that can rotate around deformation points such as connection points C in both pitch and yaw directions. In some embodiments, other degrees of freedom such as stretch and roll may be accommodated. In other embodiments, joints or other types of deformation points may be located along the lengths of the links L1-L10 to allow multiple locations for bending along the length of the links. In some embodiments, the deformation points may be distributed throughout the modeled links L1-L10, without regard to the location of connection points.

To deform the model 300 and correct for the forces applied by the catheter, the shape of the whole catheter on the bronchial passageways is determined. A shape sensor system, such as the shape sensor system 138 may be used to determine the shape of the entire catheter, not just the tip. The shape of the catheter is used to determine a set of deformation variables (e.g., pitch and yaw angles) at each connection point C in the undeformed model. The methods used to convert the modeled pitch and yaw angles of the connection points to the poses of the links in the bronchial structure are standard kinematic methods found, for example in Siciliano et al., *Springer Handbook of Robotics* (Springer, 2008). The amount of deformation of the bronchial passageways is determined by virtual forces caused by points of the catheter outside the passageways in the undeformed model. These forces effectively act to pull the passageway in the direction of the catheter. The amount of deformation is also determined by counteracting forces, such as the rigidity of the bronchial passageway and the surrounding connective tissue, which bias the passageway toward the undeformed shape and configuration.

Figure 5B:
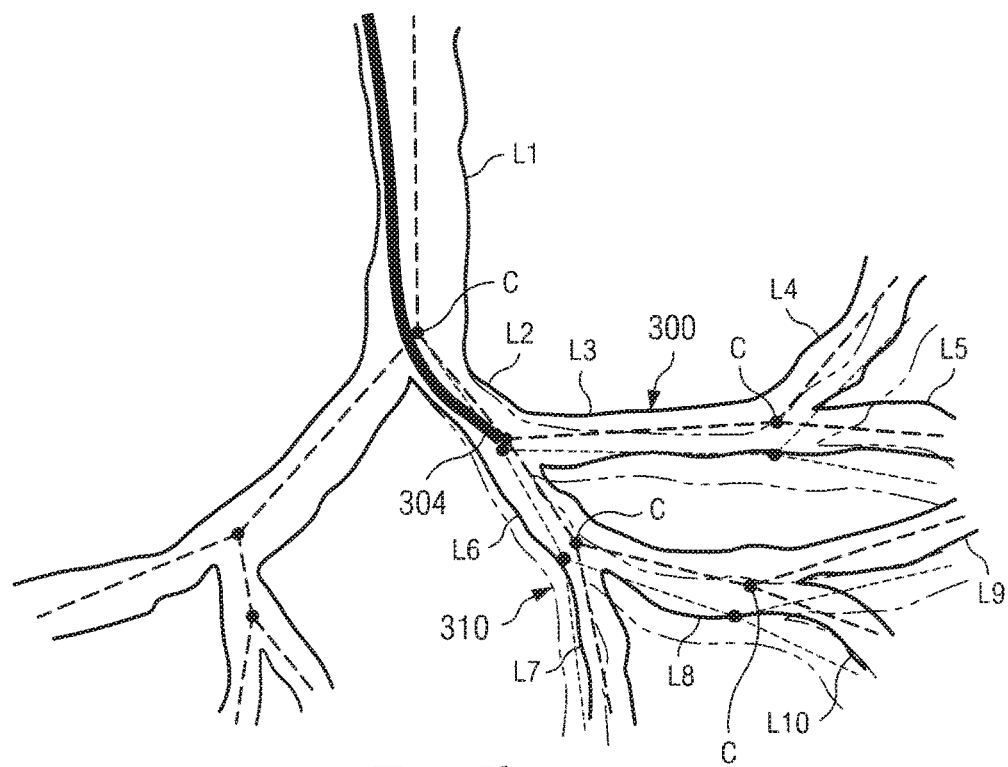
FIGS. 5b-5d illustrate composite images of the model of the bronchial passageway adjusted with the advancement of the catheter.
Figure 5C:
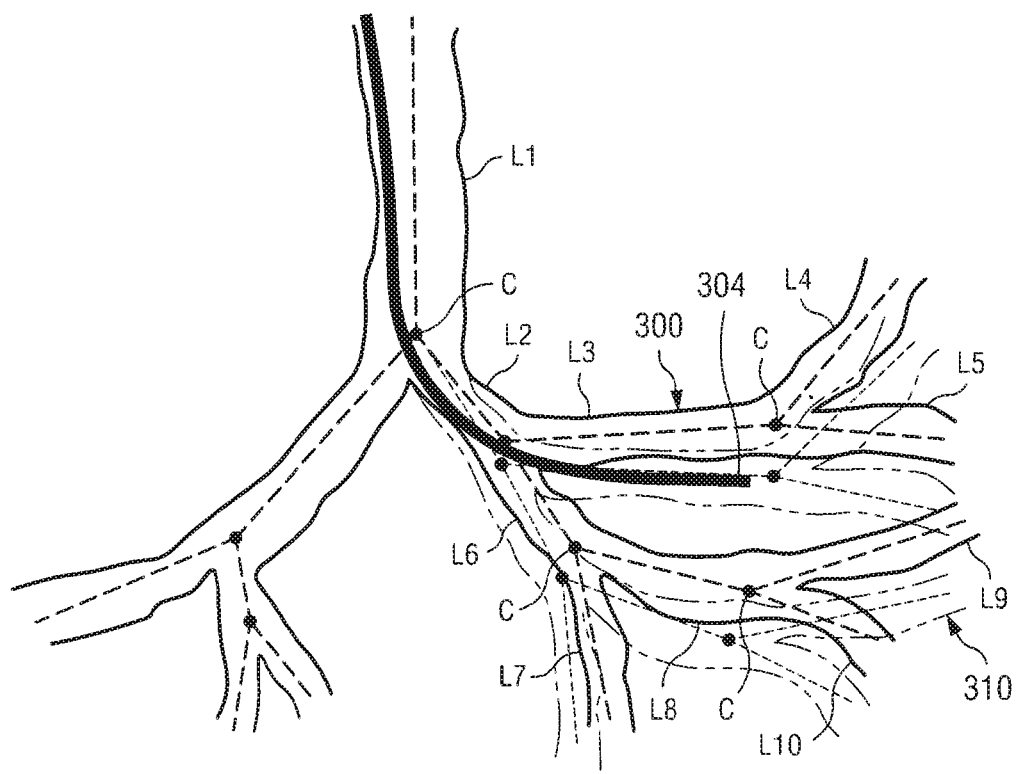
Figure 5D:
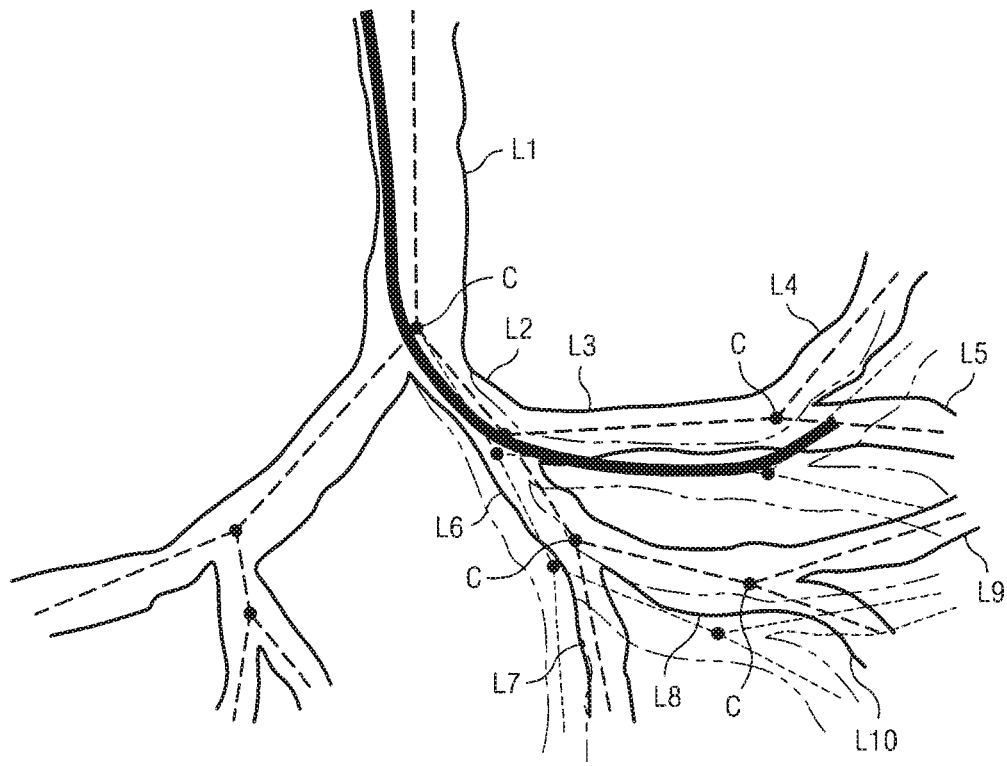
Figure 6:
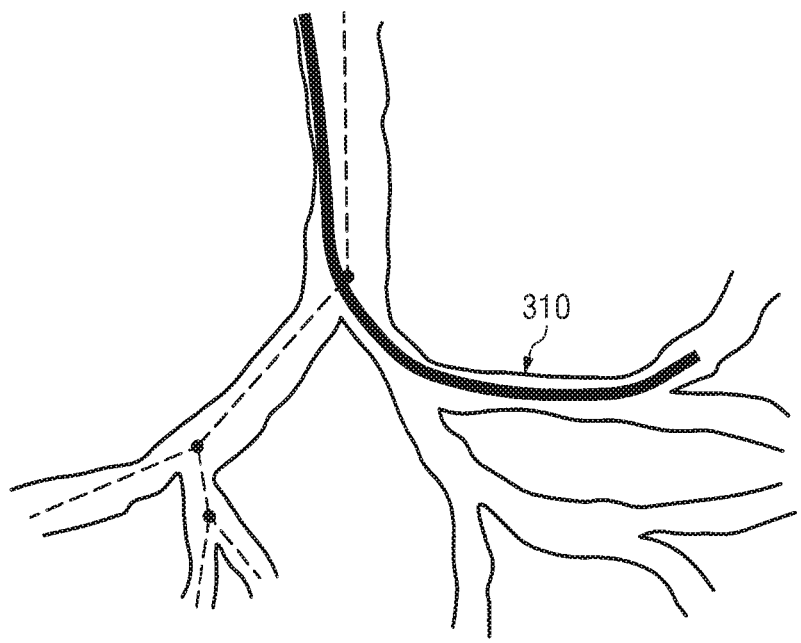
FIG. 6 illustrates a composite image of a deformed model of the bronchial passageway and catheter.

FIGS. 5b-5d depict the undeformed model 300 of the branched bronchial passageways and also shows a deformation model 310 of the branched bronchial passageways as the catheter 302 is advanced through the passageways. In FIG. 5b, the catheter 302 is advanced through link L1 and into link L2. The deformation model 310 is shifted slightly from the undeformed model 300 to adjust for the direct forces of the catheter 302 on the links L1, L2 and indirect forces on the connected distal links L3-L10. The tip 304 is depicted as within the link L2 in both the undeformed model 300 and the deformed model 310, but the exact location of the tip 304 within the link L2 is different between the two models. In FIG. 5c, the catheter 302 is advanced through link L2 and into link L3. The deformation model 310 is further shifted from the undeformed model 300 to adjust for the direct forces of the catheter 302 on the links L1, L2, L3 and indirect forces on the connected distal links L4-L10. The tip 304 is depicted as outside the link L3 in the undeformed model 300 but within the link L3 in the deformed model 310. Thus, the deformed model 310 more accurately reflects the reality that the tip 304 is inside the bronchial passageway. In FIG. 5d, the catheter 302 is advanced into link L4. The deformation model 310 is further shifted from the undeformed model 300 to adjust for the direct forces of the catheter 302 on the links L1, L2, L3, L4 and indirect forces on the connected distal links L5-L10. The tip 304 is depicted in link L5 in the undeformed model 300 and inside the link L4 in the deformed model 310. Thus, the deformed model 310 more accurately reflects the actual location of the tip 304. The final deformed model 310 is depicted in FIG. 6.

Figure 7:
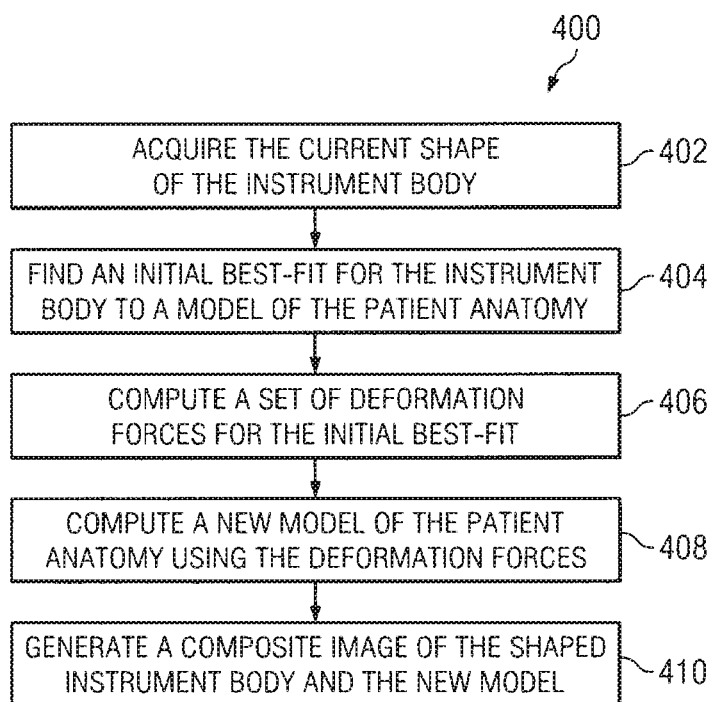
FIG. 7 is a flowchart illustrating a method for deforming a model of the bronchial passageways based upon the shape of the catheter.

One embodiment of a method for correcting an undeformed model into an adjusted or deformed model is provided in the flowchart 400 of FIG. 7. The model may be generated from stored data describing the patient anatomy, for example, from preoperative images, from two or three dimensional datasets describing the patient anatomy, from a standard (i.e., not patient specific model), or from hybrids of any of the above. Initially the deformed model is equal to the static, undeformed model with all deformation variables (e.g., pitch/yaw angles, stretch) set at zero. At step 402, the current shape of a catheter of a surgical instrument or another type of sensed device is acquired using one or more sensors of the sensor system. At step 404, a sampling of points along the shaped catheter relative to the deformed model are matched for a best-fit. During this initial iteration of the compensation cycle, the deformed model is equal to the static model. In greater detail, this best-fit matching technique may, in one example embodiment, include a) finding N links L that are closest to the tip of the catheter; b) for each of the N links L, computing the unique subset of links that form a path from that link to the base of the bronchial structure; c) for each of the N subsets, computing the closest points on the bronchial passageway to each of the sampled points along the catheter shape; d) computing a distance score for each of the N options as a function of the distances of the sampled points to the corresponding closest points in the bronchial passageway; and choosing the best option from the N options based on the lowest combined distance score.

At step 406, a set of deformation forces for the selected best fit are calculated. For each of the sampled points along the catheter shape, a force is defined as the vector between the position of the point and the position of the closest point on the bronchial passageway. Optionally, a set of restorative forces may be computed that correspond to the forces that bias the bronchial passageway toward its original shape. These restorative forces are defined between sampled point on the deformed bronchial passageway links and corresponding points on the undeformed links. Also optionally, a set of maintenance forces may be computed that correspond to the forces that bias the local shape to the undeformed local shape. These maintenance forces can be defined, for example, as joint torques acting between each pair of connected links with torque equal and opposite to the deformation angle at that connection. The total set of forces acting on the branched structure of bronchial passageways is computed as a weighted sum of the sets of deforming and restorative forces. Weight factors may be determined by a user or set in a way that results in the most realistic behavior, for example based on measured mechanical properties of the anatomy. The tissue's elasto-static properties can also be pre-estimated in multi-dimensional diagnostic images (e.g., 3D or 4D CT) possibly also involving real patient image databases for intensity to elasticity calibration. Since the CT imaging modality captures relative tissue density, a mapping between the image intensities and a tissue site's elastic properties can be pre-computed. During run time, tissue deformation under forces of known magnitude and direction can be computed to reflect a more physically accurate tissue behavior.

At step 408, a new deformed model of the bronchial passageways is computed by adjusting each joint between the bronchial passageway links by an amount proportional to the total applied torque at the joint.

At step 410, a composite image of the deformed model and the catheter is generated to accurately depict the location of the catheter within the branched structure of the bronchial passageways. Additionally, with a tip of the catheter registered to the correct link in the deformed model, a correct virtual navigation view can be retrieved from the preoperatively stored images. The process may be repeated from step 402 until the catheter reaches its desired target within the bronchial structure.

Figure 8:
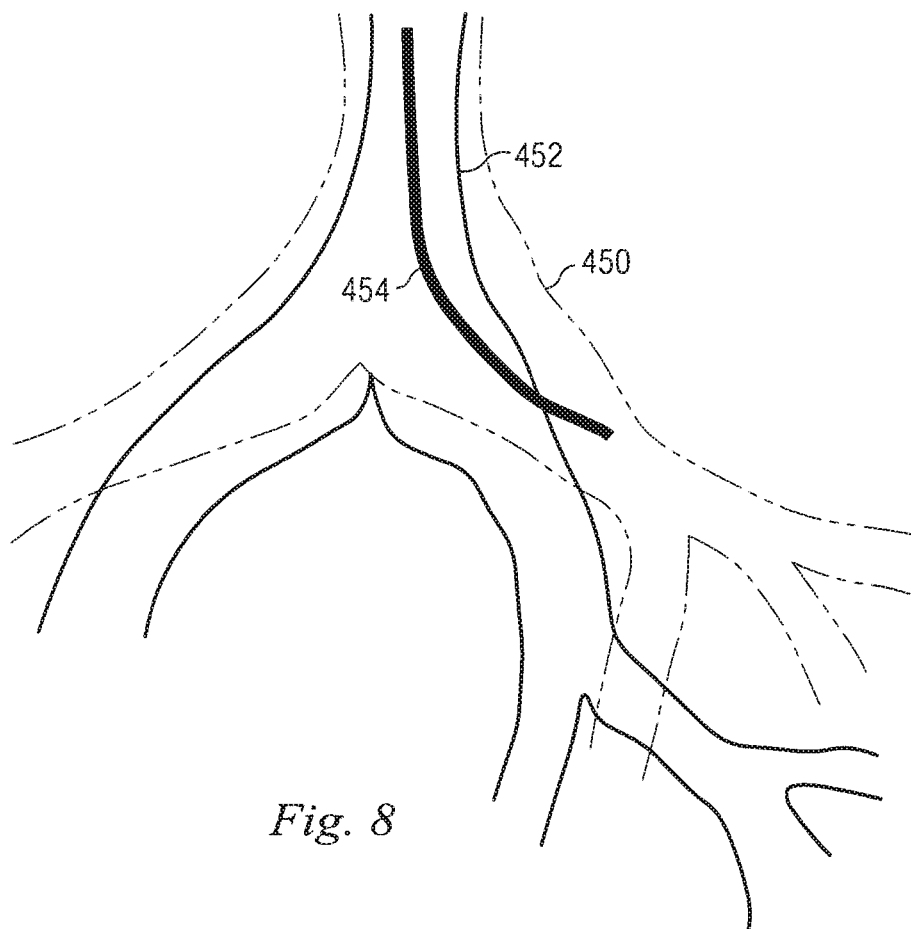
FIG. 8 is an illustration of a model of a bronchial passageway of a lung in states of expiration and inspiration.
Figure 9:
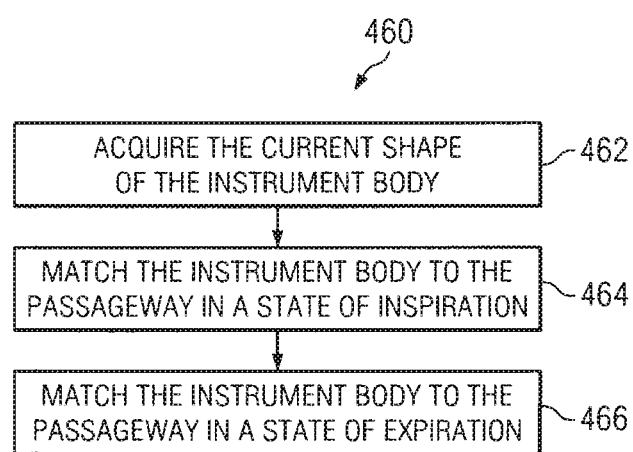
FIG. 9 is a flowchart illustrating a method of deforming a model of the bronchial passageway for states of inspiration and expiration.

In another embodiment, the non-static nature of the branched bronchial structure can be shown in an inspiration model of the bronchial structure that corresponds to an inhalation state of the bronchial structure and an expiration model that corresponds to an exhalation state of the bronchial structure. With reference to FIG. 8, the pose, position, or orientation of a catheter already adjusted based upon a sensor system can be further refined or warped to the shape of a bronchial passageway as the passageway adjusts between a state of inspiration and expiration and vice versa. FIG. 8 depicts an inspiration model 450 and an expiration model 452. A catheter 454 is initially located based upon the sensor system but is adjusted to remain within the image of the bronchial passageways as they move between states of inspiration and expiration. FIG. 9 is a flow chart 460 describing a method for adjusting the catheter based on states of inspiration and expiration. At step 462, the current shape of the catheter is acquired. At step 464, the catheter shape is matched to the shape of the bronchial passageway in a state of inspiration. At step 466, the catheter shape is matched to the shape of the bronchial passageway in a state of expiration. In a composite image of the bronchial passageways and the catheter, the image of the catheter is maintained within the bronchial passageways for each state of expiration and inspiration. The process may be repeated until the catheter reaches its desired target within the bronchial structure. In alternative embodiments, the process may be used to correct images for any instrument located within any moving anatomical structure, and in particular an anatomic structure, such as the heart or lungs, that repeatedly alternates between known states. For example, the moving anatomical structure may be a heart alternating between diastole and systole phases of the cardiac cycle.

In alternative embodiments, the instruments or the anatomic passageways may be modeled using three dimensional shape histograms to perform similarity searching. For example, a metric may be developed to measure similarity between two three-dimensional curves. With reference to FIG. 10, a curve 500 corresponds to a measured device path through a reference anatomy and a curve 502 corresponds to an actual anatomic passageway. For each point $P_i$ on these curves, the following parameters may be defined: a) local gradient, b) local curvature, c) radial angular displacement with respect to an endpoint connector, d) radial distance with respect to an endpoint connector, e) radial angular/displacements with respect to a third reference axis 504. As shown in FIG. 11, a histogram 505 may be created from each of the above parameters. The histograms are matched directly to create a metric for each curve similarity.

In another embodiment, an arbitrarily shaped point set is snapped to another point set using a metric to measure the quality of the match. With reference to FIG. 12, two point sets $P_T$ and $P_S$ are provided. Starting with $P_S$, a similarity measure $|S_{S \to T}|$ is computed. The similarity measure is a one dimensional histogram indexed on distance from a reference point. The value of a tangent vector at the reference point is stored with respect to a reference vector. An optimizer is used to optimize the degrees of freedom on a transform to maximize the similarity measure at an instant between $P_S$ and $P_T$.

Alternative systems and methods for registering an image of at least a portion of a flexible instrument to an image of an anatomical system are disclosed in U.S. patent application Ser. No. 13/893,040, entitled "Systems and Methods for Registration of a Medical Device Using a Reduced Search Space" and in U.S. patent application Ser. No. 13/892,924, entitled "Systems and Methods for Registration of a Medical Device Using Rapid Pose Search," both of which are incorporated by reference herein in their entirety. Aspects of theses incorporated by reference systems and methods may be used together with the above disclosed systems and methods to provide alternative methods of accurately registering an image of at least a portion of a flexible instrument to an image of an anatomical system.

Although the registration systems and methods have been described herein with respect to teleoperated or hand operated surgical systems, these registration systems and methods will find application in a variety of medical and non-medical instruments in which accurate instrument image registration is otherwise too time consuming or computer processing intensive.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
   a surgical device including a tracking system disposed along a length of an elongate flexible body of the surgical device; and
   a processor configured for:
   receiving a first model of anatomic passageways of a patient anatomy, the first model including a set of model passageways representing a proximal branch of the patient anatomy connected to a distal branch of the patient anatomy;
   receiving from the tracking system a shape of the elongate flexible body of the surgical device positioned within the proximal branch and the distal branch of the patient anatomy;
   determining, based on the shape of the elongate flexible body, a set of forces acting on the patient anatomy in response to the surgical device positioned within the proximal branch and the distal branch;
   generating a second model of the patient anatomy by deforming the first model based on the determined set of forces; and
   displaying a representation of the second model and a representation of the elongate flexible body as positioned within the second model.

2. The medical system of claim 1, wherein the tracking system includes an optical fiber shape sensor disposed along the length of the elongate flexible body.

3. The medical system of claim 1 wherein the tracking system includes a plurality of electromagnetic sensors disposed along the length of the elongate flexible body.

4. The medical system of claim 1 wherein displaying the second model and the representation of the elongate flexible body includes displaying the representation of the elongate flexible body as extending within a deformed set of the model passageways representing the proximal and distal branches of the patient anatomy.

5. The medical system of claim 1 wherein the processor is further configured for fitting a sampling of points along the shape of the elongate flexible body of the surgical device to the first model wherein the tracking system disposed along the length of the elongate flexible body produces the sampling of points.

6. The medical system of claim 1 wherein determining the set of forces includes determining a set of deformation forces exerted by the elongate flexible body on at least one anatomic passageway.

7. The medical system of claim 1 wherein determining the set of forces includes determining a set of restorative forces that bias the anatomic passageways toward an original shape.

8. The medical system of claim 1 wherein determining the set of forces includes determining a set of maintenance forces, each maintenance force of the set of maintenance forces represented as a joint torque acting opposite to a deformation angle at a connection point of two of the anatomic passageways.

9. The medical system of claim 1 wherein determining the set of forces includes determining a weighted sum of a set of deformation, restorative, and maintenance forces.

10. The medical system of claim 1 wherein determining the set of forces includes determining elastic properties for the anatomic passageways.

11. The medical system of claim 10 elastic properties for the anatomic passageways are determined from tissue densities obtained from a set of anatomical data used to generate the first model.

12. The medical system of claim 1 wherein the processor is further configured for:
    determining a location of a distal end of the representation of the elongate flexible body relative to the second model; and
    generating a virtual navigation view of the anatomic passageways based on the determined location of a distal end of the representation of the elongate flexible body.

13. A medical system comprising:
    a surgical device; and
    a processor configured for:
        generating a first model of a plurality of branched anatomical passageways from stored anatomical data describing a patient anatomy recorded while the branched anatomical passageways are in a first state of an alternating movement, wherein the plurality of branched anatomical passageways includes a proximal branch connected to a distal branch;
        generating a second model of the plurality of branched anatomical passageways from stored anatomical data describing a patient anatomy recorded while the branched anatomical passageways are in a second state of the alternating movement;
        generating a first image of the surgical device in a first shape extending within the proximal branch and the distal branch of the first model of the plurality of branched anatomical passageways when the branched anatomical passageways are in the first state;
        generating a second image of the surgical device in a second shape extending within the proximal branch and the distal branch of the second model of the plurality of branched anatomical passageways when the branched anatomical passageways are in the second state; and
        determining, based on the first shape, a set of forces acting on the branched anatomical passageways in response to the surgical device extending within the proximal branch and the distal branch.

14. The medical system of claim 13 wherein the surgical device includes a tracking system disposed along a length of an elongate flexible body of the surgical device and wherein the processor is further configured for receiving, from the tracking system, shape information for determining the first shape.

15. The medical system of claim 14, wherein the tracking system includes an optical fiber shape sensor disposed along the length of the elongate flexible body.

16. The medical system of claim 14 wherein the tracking system includes a plurality of electromagnetic sensors disposed along the length of the elongate flexible body.

17. The medical system of claim 13 wherein the branched anatomical passageways are bronchial passageways and the first state is a state of expiration and the second state is a state of inspiration.

18. The medical system of claim 13 wherein the branched anatomical passageways are cardiac passageways and the first state is a diastole phase of a cardiac cycle and the second state is a systole phase of the cardiac cycle.

19. The medical system of claim 13 wherein the processor is further configured for:
    generating a third image of the surgical device in a refined shape positioned within a refined model of the plurality of branched anatomical passageways when the branched anatomical passageways are in a third state, wherein the refined shape is obtained by combining the first and second shapes and the refined model is obtained by combining the stored anatomical data from the first and second states.

20. The medical system of claim 13 wherein determining the set of forces includes determining a set of deformation forces exerted by the surgical device on at least one anatomic passageway.

* * * * *

UNITED STATES PATENT AND TRADEMARK OFFICE
CERTIFICATE OF CORRECTION

| | |
|---|---|
| PATENT NO. | : 11,678,813 B2 |
| APPLICATION NO. | : 17/240154 |
| DATED | : June 20, 2023 |
| INVENTOR(S) | : Vincent Duindam, Prashant Chopra and Tao Zhao |

It is certified that error appears in the above-identified patent and that said Letters Patent is hereby corrected as shown below:

On the Title Page

Item (57) should read as follows:
-- A medical system may comprise a processor and a surgical device including a tracking system disposed along a length of an elongate flexible body. The processor may receive a first model of anatomic passageways of a patient anatomy. The first model may include a set of model passageways representing proximal and distal branches. The processor may also receive from the tracking system a shape of the elongate flexible body positioned within the proximal and distal branches. The processor may also determine, based on the shape of the elongate flexible body, a set of forces acting on the patient anatomy in response to the surgical device positioned within the proximal and distal branches. The processor may also generate a second model by deforming the first model based on the set of forces and display the second model and a representation of the elongate flexible body within the second model. --

Signed and Sealed this
Twenty-second Day of August, 2023

Katherine Kelly Vidal
*Director of the United States Patent and Trademark Office*